United States Patent
Allen

(10) Patent No.: US 11,712,269 B2
(45) Date of Patent: Aug. 1, 2023

(54) ADJUSTABLE, MODULAR INSTRUMENT AND METHOD FOR SPINAL MANIPULATION

(71) Applicant: GLOBUS MEDICAL, INC., Audubon, PA (US)

(72) Inventor: Caelan Allen, Philadelphia, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 17/546,201

(22) Filed: Dec. 9, 2021

(65) Prior Publication Data

US 2023/0181224 A1 Jun. 15, 2023

(51) Int. Cl.
*A61B 17/70* (2006.01)
*A61B 17/68* (2006.01)

(52) U.S. Cl.
CPC ...... *A61B 17/7032* (2013.01); *A61B 17/7019* (2013.01); *A61B 17/7023* (2013.01); *A61B 17/7082* (2013.01); *A61B 2017/681* (2013.01)

(58) Field of Classification Search
None
See application file for complete search history.

(56) References Cited

U.S. PATENT DOCUMENTS

| | | | | |
|---|---|---|---|---|
| 9,402,660 B2* | 8/2016 | Brinkman | | A61B 17/7077 |
| 9,770,272 B2* | 9/2017 | Thoren | | A61B 17/7077 |
| 2013/0289633 A1* | 10/2013 | Gleeson | | A61B 17/7074 |
| | | | | 606/86 A |
| 2015/0066088 A1* | 3/2015 | Brinkman | | A61B 17/7077 |
| | | | | 606/264 |
| 2015/0105831 A1* | 4/2015 | Yim | | A61B 17/7091 |
| | | | | 606/86 A |
| 2015/0320458 A1* | 11/2015 | Rezach | | A61B 17/7085 |
| | | | | 606/279 |

* cited by examiner

*Primary Examiner* — Tessa M Matthews

(57) ABSTRACT

A spinal manipulation instrument, system, and method may use a driving rod to move instrument arms toward or away from one another to compress or distract between selected vertebrae to which the arms are connected. Two arms may be coupled to the driving rod. A threaded collar may axially engage one of the arms, to translate that arm along the driving rod with respect to the other arm. The other arm may be at a fixed axial location or driven by another, oppositely-oriented thread. The arms may be highly adjustable to accommodate a wide range of anatomical variation between patients. Attachment members may be modular to interchangeably couple the arms across multiple platforms.

5 Claims, 5 Drawing Sheets

ADJUSTABLE, MODULAR INSTRUMENT AND METHOD FOR SPINAL MANIPULATION

BACKGROUND

Spinal irregularities can result from a variety of factors, such as trauma, disc degeneration, tumors, and other forms of disease. These irregularities can cause pain, limit range of motion, or injure the nervous system within the spinal column. Procedures have been developed to correct or mitigate spinal irregularities, such as by repairing or replacing affected tissues along the spine and/or installing implants such as spinal fixation devices. Such procedures generally require manipulating, at least temporarily, the individual vertebrae around the affected area. Because of the complexity of the spine and the relatively fragile spinal structures it comprises, the instruments and techniques involved should be reliable and capable of precision.

SUMMARY

In an example embodiment, a spinal manipulation instrument comprises a driving rod with a threaded portion defining an axis therethrough. A first arm is rotatably coupled to the driving rod about the axis. A second arm is also rotatably coupled to the driving rod about the axis. A threaded collar is coupled to the threaded portion of the driving rod in axial engagement with the second arm, such that the second arm translates along the driving rod with respect to the first arm in response to the rotation of the driving rod about the axis. Pedicle connectors are configured for releasably coupling the first and second arm to respective vertebra.

In another example embodiment, a spinal manipulation instrument, comprises a driving rod with a threaded portion defining an axis therethrough. A first arm is rotatably coupled to the driving rod about the axis at a fixed axial location along the driving rod, such that the first arm remains at the fixed axial location during a rotation of the driving rod about the axis. A second arm includes a threaded collar coupling the second arm to the threaded portion of the driving rod, such that the second arm translates along the driving rod with respect to the first arm in response to the rotation of the driving rod about the axis. A pivot mount between at least one of the first and second arms and the driving rod allows the arm(s) to pivot with respect to the other. Pedicle connectors configured for releasably coupling each of the first and second arm to a respective bone fastener include a connector tip on each of the first and second arms. The pedicle connectors also include a plurality of modular attachment members of different attachment member configurations for interchangeably coupling one of the connector tips to the respective bone fastener. A swivel is also included, allowing rotation of each attachment member about an axis of the respective first or second arm, wherein the swivel is lockable at any of a plurality of different swivel angles within a 360-degree swivel range.

In another example embodiment, a method comprises releasably coupling distal ends of first and second arms of an instrument to respective vertebrae, wherein proximate ends of the first and second arms are rotatably coupled to a driving rod about an axis defined by a threaded portion of the driving rod. The driving rod is rotated with the threaded portion of the driving rod coupled with a threaded collar in axial engagement with the second arm, to translate the second arm along the driving rod with respect to the first arm.

The foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

These drawings illustrate certain aspects of some of the embodiments of the present disclosure and should not be used to limit or define the method.

DETAILED DESCRIPTION

Figure 1:
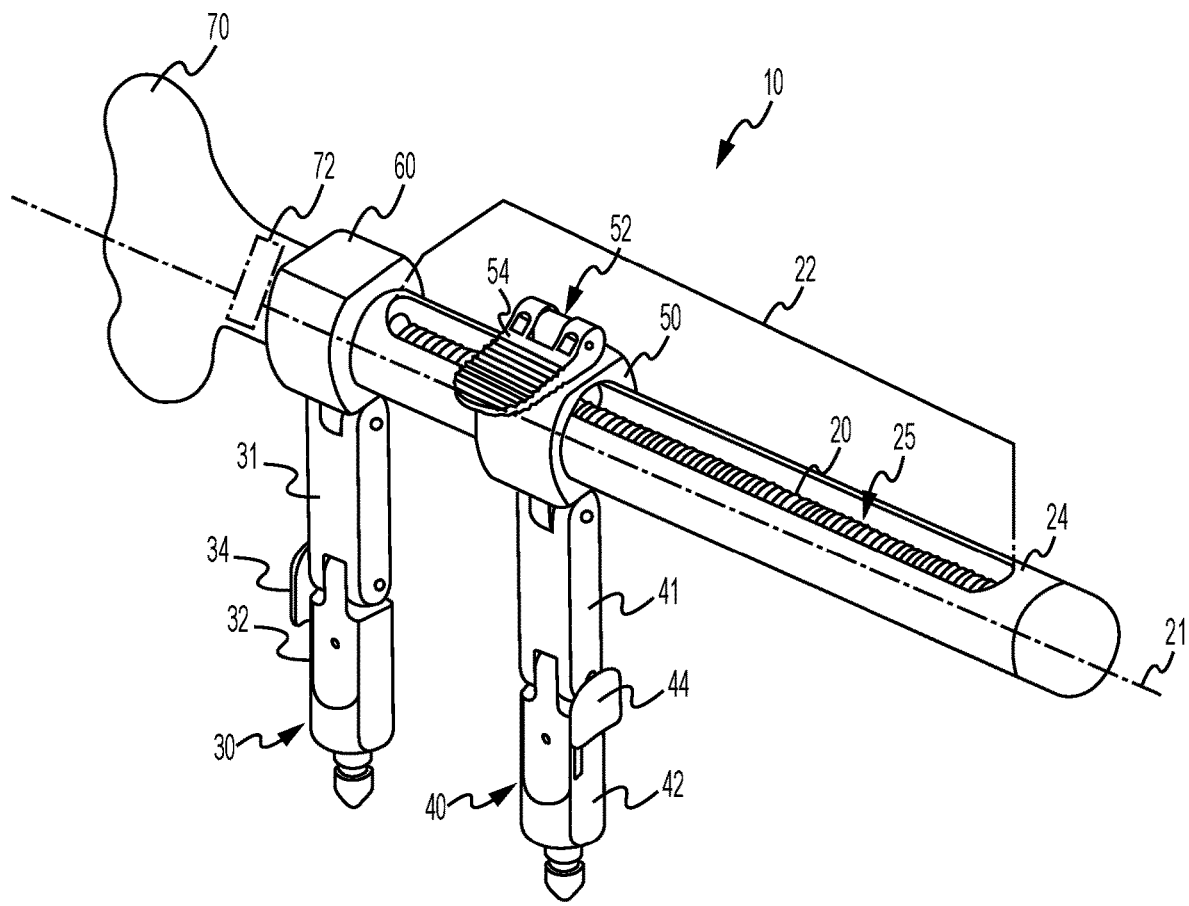
FIG. 1 is a perspective view of a surgical instrument according to one example configuration.

A surgical instrument and method are disclosed for manipulating vertebrae during spinal surgery. In any of a variety of embodiments, the instrument generally includes first and second arms for coupling to respective vertebra with pedicle connectors. In a minimally invasive type spinal surgery, for example, one or more bone fastener (e.g., a pedicle screw) may be embedded in each vertebra to be manipulated. Then, the pedicle connectors may be used to releasably couple the arms of the instrument to the bone fasteners. The arms may be adjusted to conform to the particular positions of the vertebrae to which they are coupled. The arms may then be driven toward or apart from one another by rotation of a driving rod, to alternately compress or distract the vertebrae. The threaded operation to move the arms in linear translation provides a very strong and robust instrument to properly compress and distract. The adjustability of the instrument, such as using articulating, swiveling, and/or multi-segmented arms, allows the disclosed surgical instrument to better conform to a wider variation of anatomy as compared with previously existing instruments.

In disclosed examples, a threaded collar is coupled to a threaded portion of the driving rod, so that relative rotation between the driving rod and the threaded collar drives the threaded collar axially along the driving rod. The threaded collar is in engagement with at least one of the arms, i.e., a mobile arm of the instrument, to translate the mobile arm along the rod in response to the rotation of the driving rod. The fixed arm may be rotatably coupled to the driving rod at a fixed (e.g., non-threaded) axial location, so that the other, mobile arm is moved toward or away from the fixed arm in response to rotation of the driving rod. An alternate configuration may have two mobile arms that are driven in opposite directions using threaded collars of opposite threading. In either case, the rod may be rotated in one rotational direction to urge the arms and the connected vertebrae apart (distraction), and in the other rotational direction to urge the arms and the connected vertebrae toward one another (compression). In some embodiments, the threaded collar is releasably coupled to the threaded portion of the driving rod, to allow the associated arm to slide along the driving rod without rod rotation before re-engaging the threaded collar with the threaded portion of the driving rod. This may facilitate a stress-free initial connection of the arms to the vertebrae.

The surgical instrument includes several optional features that may be included alone or in combination to accommodate anatomical variations, such as the height and angle between pedicles. For example, one or both arms may be capable of articulation with respect to the driving rod, such as with pivot mounts between the arms and the driving rod. One or both arms may also be capable of swiveling about their individual arm axes, such as with a lockable swivel. The arms may be double jointed, each comprising multiple arm segments pivotally connected end to end, allowing for an adjustable arm length and/or adjustable angle between arm segments. The system may also be modular, allowing the instrument to be used across multiple platforms of different connection types. For example, a modular system may include modular attachment members comprising a variety of different (i.e., two or more) attachment member configurations for interchangeably coupling to the respective bone fastener. These and other features and principles are disclosed by way of non-limiting examples represented in the figures. The various embodiments may also include multi-level or single level instrumentation. Multi-level instrumentation may have an increased length of travel, allowing the mobile arm to span across one or more vertebrae. A single level instrument may have a decreased travel length, such that it would not take up unnecessary working room during use. A single level instrument may also have a more traditional squeeze handle method of actuation for compression/distraction, but would retain the same modularity of connectors.

FIG. 1 is a perspective view of a surgical instrument 10 according to one example configuration, including a non-limiting combination of adjustment features described below. The instrument includes first and second arm 30, 40 for coupling to respective vertebrae. The first arm 30 is a fixed arm and the second arm 40 is a mobile arm in this example. The surgical instrument 10 also includes a driving rod 20 rotatable about a central axis 21 within and by a rod housing 24. The rod 20 includes a threaded portion 22 along at least a portion of its length about the axis 21. The rod housing 24 includes an elongate opening 25 to expose the threaded portion 22 for engagement by other threaded features discussed below. Proximate ends of the first and second arms 30, 40 are rotatably coupled to the rod 20 at different axial locations along the rod 20, and distal ends of the arms 30, 40 may be coupled to vertebrae, so that the rod 20 may rotate with respect to the arms 30, 40 to alternately compress or distract the vertebrae. A threaded collar 50 threadedly engages the threaded portion 22 of the rod 20, such as with an inner thread (not explicitly shown), so that rotation of the rod 20 advances the threaded collar 50 axially along the rod 20. Although it can be desirable for the threaded collar 50 to fully encircle the threaded rod and rod housing as shown, a threaded collar as described herein need not fully encircle the threaded rod so long as it threadedly engages enough of the threaded portion 22 of the rod to be urged axially in response to rotation of the driving rod 20. The threaded collar 50 engages the second arm 40 such that the second arm translates along the driving rod with respect to the first arm 30 in response to rotation of the driving rod 20 about the axis 21. In this example, more particularly, the threaded collar 50 is coupled between an end of the second arm 40 and the rod housing 24. In an alternate embodiment, the threaded collar 50 could instead be positioned elsewhere on the rod 20, such as adjacent to (on either or both sides of) the second arm 40 and be coupled with or otherwise engage the second arm 40 to urge the second arm 40 in either axial direction.

The first arm 30 is coupled to the driving rod 20 but without threadedly engaging the threaded portion 22 of the rod 20. For example, the first arm 30 may be coupled to the rod housing 24 with a non-threaded collar 60, which in turn is coupled to the driving rod 20 (the term "couple" includes direct or indirect coupling in this context). Thus, in this example, the first arm 30 is rotatably coupled to the driving rod 20 at a fixed axial location along the driving rod 20, so that the first arm 30 remains at the fixed axial location while the second arm 40 may translate with respect to the first arm 30 by rotation of the driving rod 20. In this context, the first arm 30 may, again, be referred to as the fixed arm and the second arm 40 may be referred to as the mobile arm.

In an alternate embodiment, both arms 30, 40 could be mobile. For example, the driving rod 20 could include another threaded portion that is oppositely oriented (i.e., reverse threading) from the threaded portion 22 shown, and another threaded collar could be engageable with such other threaded portion, so that rotation of the driving rod 20 urges the first and second arms 30, 40 in opposite axial directions. In either configuration (i.e., whether the first arm is fixed or mobile), rotating the rod 20 in one rotational direction urges the arms 30, 40 apart relative to one another for distraction of the connected vertebrae and rotating the rod 20 in the opposite rotational direction urges the arms 30, 40 toward one another for compression of the connected vertebrae.

FIG. 1 also illustrates a number of optional adjustment features to help conform to anatomical differences, such as different angles and spacings between vertebrae. One adjustment feature is segmented arms. In this example, the first arm 30 is double-jointed, comprising two arm segments 31, 32 connected end to end. Likewise, the second arm 40 is double-jointed comprising two arm segments 41, 42 connected end to end. The arm segments 31, 32 and 41, 42 are coupled to one another allowing a positional adjustment between the arms segments 31, 32 of the first arm 30 and between the arm segments 41, 42 of the second arm 40. In this example, the arm segments 31, 32 are pivotably coupled to one another at adjacent ends to allow the arm segments 31, 32 to be pivoted with respect to each other. Likewise, the arm segments 41, 42 are pivotably coupled to one another at adjacent ends to allow the arm segments 41, 42 to be pivoted with respect to each other. In an alternate configuration, the arm segments of each arm could be telescopically coupled to one another to adjust an overall length of each arm 30, 40. Once an adjustment has been made (e.g., pivoting or telescoping) between arm segments, a cam lever 34, 44 or other locking feature may be engaged to lock the arm segments in that relative position. Note that the cam levers 34, 44 or other features may alternatively be used to lock a lockable swivel as described below.

Another adjustment feature in FIG. 1 is a releasable threaded connection 52 between the threaded collar 50 and the threaded portion 22 of the driving rod. The releasable threaded connection 52 allows for non-threaded axial repositioning of the second arm 40 along the driving rod 20. In FIG. 1, a cam lever 54 is shown in a latched position that threadedly engages the threaded collar 50 with the threaded portion 22 of the driving rod 20. The threaded connection between the threaded collar 50 and the threaded portion 22 of the driving rod 20 may be released by flipping the cam lever 54 in an unlocked position (upward in this example). In another embodiment, the releasable threaded connection comprises a spring-loaded button, or other suitable mechanism for releasably coupling the threaded collar 50 to the threaded portion 22 of the driving rod 20. When released, the threaded collar is functionally disengaged from the threaded portion 22 of the driving rod 20 so that the second arm 40 may simply be slid along the driving rod 20 by hand. This releasable threaded connection is useful, for example, for making a connection between the arms 30, 40 and respective vertebrae. The first arm 30, which is secured to the driving rod 20 at a fixed axial location in this embodiment, does not include the releasable threaded connection, but other embodiments could include a releasable threaded connection on both arms 30, 40.

A driving handle 70 is included to facilitate rotation of the driving rod 20 by hand. The handle 70 may have any suitable shape. The handle provides leverage for applying torque to the driving rod 20, which is used to urge vertebrae toward or away from each other once connected to the vertebrae, as discussed below. However, to limit the amount of torque and corresponding force applied to the vertebrae, a torque limiter may be included between the handle 70 and the driving rod. A representative torque limiter 72 is schematically indicated in FIG. 1, and may include any suitable mechanism for limiting the amount of torque that may be applied. Examples of suitable torque limiters include friction-based torque limiters, detent torque limiters, digital torque limiters, magnetic torque limiters, shear pin torque limiters, pawl and spring torque limiters, etc. In other embodiments, rotation of the driving rod 20 could be performed using a motor of any suitable type. For example, an electric motor with one or more control buttons may be used to power rotation on and off and to control the rotational direction. The torque could be electronically limited or electro-mechanically limited in that case.

Figure 2:
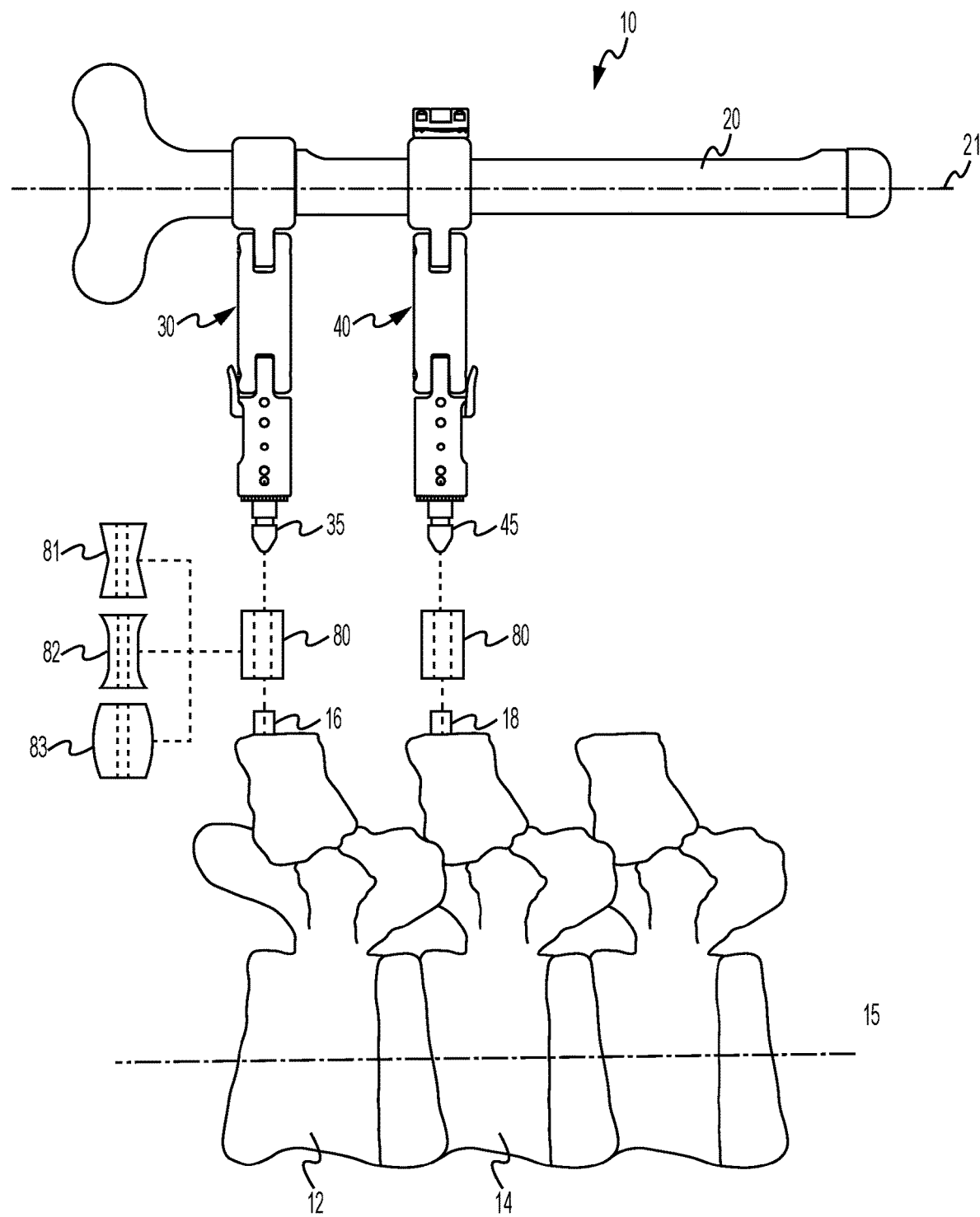
FIG. 2 is a front view of the surgical instrument schematically illustrating a releasable connection of the arms to respective vertebra.

FIG. 2 is a front view of the surgical instrument 10 of FIG. 1, schematically illustrating a releasable coupling of the arms 30, 40 to respective vertebra 12, 14 with pedicle connectors. Pedicle connectors in this embodiment comprise attachment members 80 that connect to connector tips 35, 45 and to bone fasteners 16, 18. As a schematic illustration, the figure is not necessarily to scale and is not intended to limit the surgical instrument 10 to being positioned at a specific orientation with respect to the patient's spine. As illustrated here, the arms 30, 40 extend away from a posterior end of the spine, although the surgical instrument 10 could alternatively be positionable with the arms extending in another direction. The axis 21 of the driving rod 20 may be aligned with the sagittal plane of the spine 15 so that axial translation of the arms 30, 40 urges the vertebrae 12, 14 in general alignment with the sagittal plane 15. However, depending on the configuration of the releasable connection between the arms 30, 40 and the vertebrae 12, 14 the instrument may be positioned at a different orientation than what is shown.

A bone fastener 16, 18 has been inserted into each vertebra 12, 14. The bone fasteners 16, 18 may comprise pedicle screws, screw extensions, tulip, or other suitable fastener used in spinal surgery, and these provide anchor points for releasably coupling the arms 30, 40 to the respective vertebrae 12, 14. The attachment members 80 may comprise any suitable connector type for releasably connected the arms 30, 40 to the bone fasteners 16, 18, such as by coupling one end of each attachment member 80 to a connector tip 35, 45 at a distal end of the respective arm 30, 40, and another end of each attachment member 80 to the respective bone fastener 16, 18. The surgical instrument 10 may be part of a modular system, comprising attachment members of a variety of different attachment member configurations that may be used interchangeably to couple the arms 30, 40 to the vertebrae 12, 14. The possibility of different, interchangeable attachment members is schematically illustrated at 81, 82, 83. The different attachment member configurations may have different sizes, shapes, connector types at one or both ends, and so forth. The modular configuration allows the instrument to be used across multiple platforms.

Figure 3:
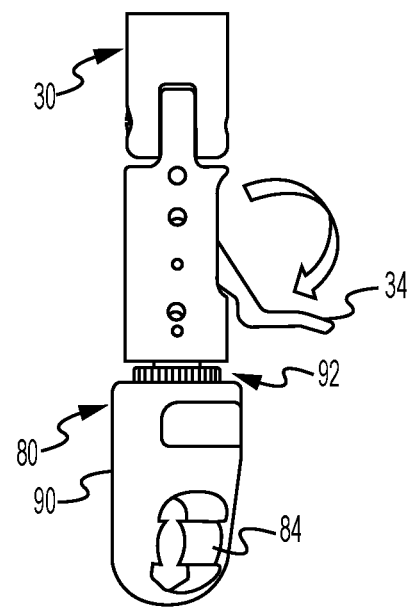
FIG. 3 is a side view of an attachment member according to an example configuration comprising a lockable swivel.

FIG. 3 is a side view of an attachment member 80 according to an example configuration comprising a lockable swivel 90. The lockable swivel 90 is in an unlocked position in FIG. 3. The swivel 90 allows for rotatably securing each attachment member 80 to the respective arm 30, 40. In the unlocked position of FIG. 3, the swivel 90 may swivel up to 360 degrees. The swivel 90 may therefore allow the arm 30 (and/or arm 40) to which it is coupled to swivel with respect to the vertebra to which it may be coupled. The swivel 90 may be lockable at any of a plurality of different swivel angles within the swivel range. In this example, the swivel 90 includes a Hirth type gear connection comprising teeth 92. The cam lever 34 is flipped to an unlocked position as indicated by the arrow to disengage the teeth 92. The attachment member 80 also comprises an aperture 84 for receiving a respective bone fastener to couple the attachment member 80 to the bone fastener.

Figure 4:
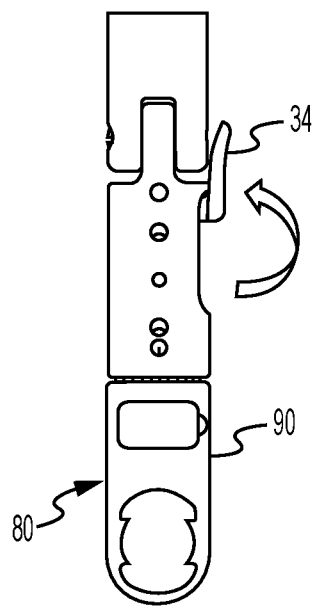
FIG. 4 is a side view of the attachment member of FIG. 3, wherein the lockable swivel has been moved to a locked position.

FIG. 4 is a side view of the attachment member 80 of FIG. 3, wherein the lockable swivel 90 has been locked by flipping the cam lever 34 to a locked position. The swivel 90 has been rotated to a selected swivel angle that is different than the swivel angle of FIG. 3. Then, with the cam lever 34 flipped to a locked position, the teeth of FIG. 3 are now engaged to lock the lockable swivel 90 in the selected swivel angle.

Figure 5:
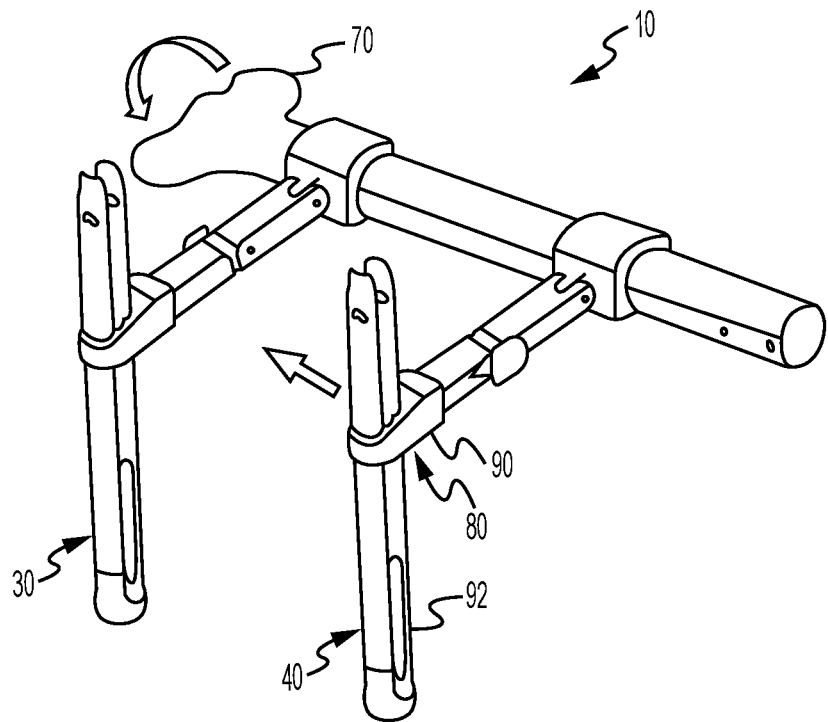
FIG. 5 is a perspective view of the surgical instrument in a compression mode of use.

FIG. 5 is a perspective view of the surgical instrument 10 in a compression mode of use, wherein the handle 70 is being turned in one rotational direction to urge the arms 30, 40 toward one another (e.g., one or both arms 30, 40 being mobile). The attachment member 80 on each arm 30, 40 includes a respective lockable swivel 90 receiving a respective bone fastener 94, each of which may be implanted in selected vertebrae (not shown). Thus, rotation of the handle 70 in the first direction will urge the two vertebrae together in compression.

Figure 6:
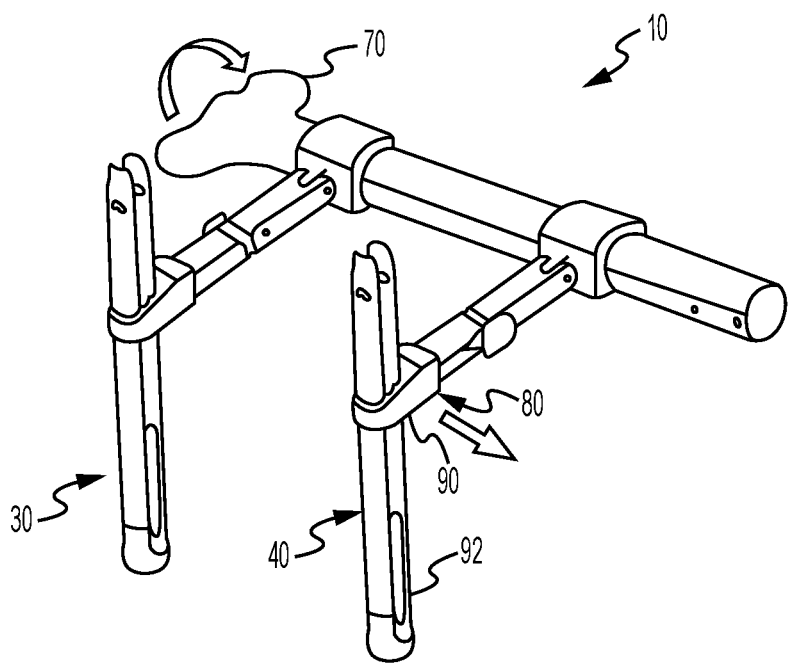
FIG. 6 is a perspective view of the surgical instrument in a distraction mode of use.

FIG. 6 is a perspective view of the surgical instrument 10 in a distraction mode of use, wherein the handle 70 is being turned in the opposite rotational direction as FIG. 5, to urge the arms 30, 40 apart from one another (e.g., one or both arms 30, 40 being mobile). The attachment member 80 on each arm 30, 40 includes the respective lockable swivel 90 receiving the respective bone fastener 94 that may be implanted in selected vertebrae. Thus, rotation of the handle 70 in the direction of FIG. 6 will urge the two vertebrae apart (distraction).

Figure 7:
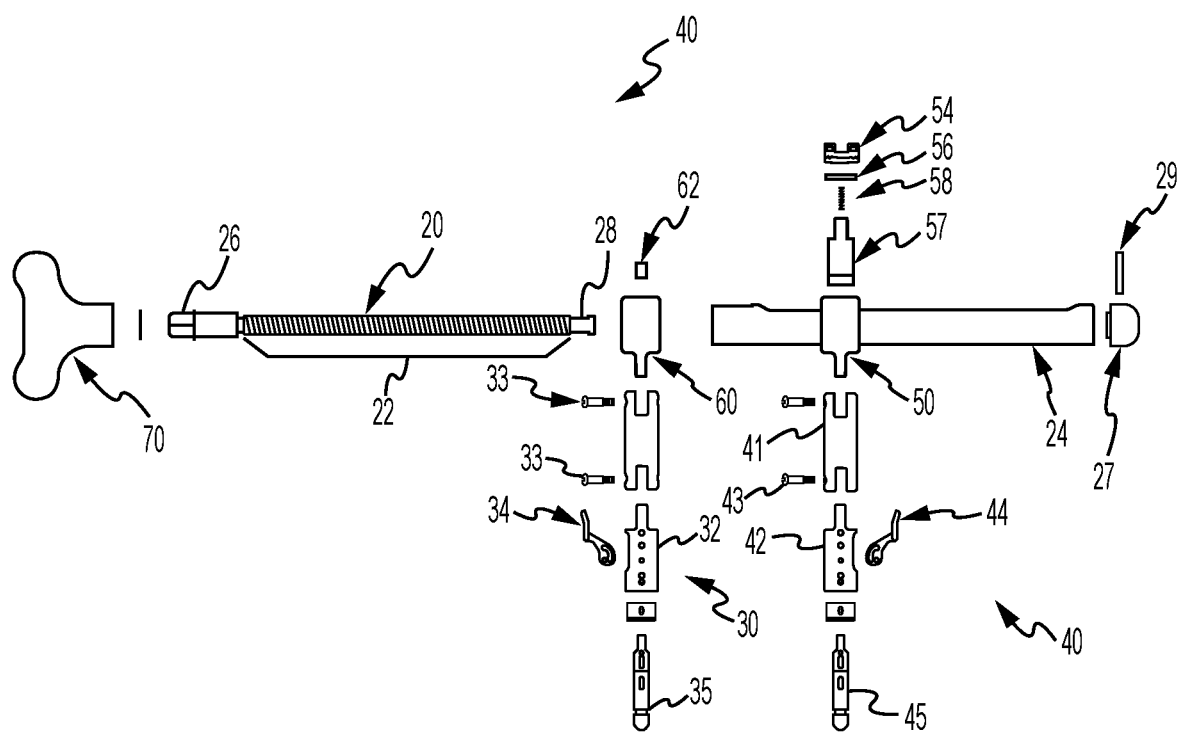
FIG. 7 is an exploded view of the surgical instrument according to one example configuration.

FIG. 7 is an exploded view of the surgical instrument 10 according to one example configuration. This view shows a non-exhaustive combination of optional adjustment features. The handle 70 may be mounted on a first end 26 of the driving rod 20, such as with a retaining ring 74 or other suitable hardware. An opposing, second end 28 of the driving rod may be inserted through the non-threaded collar 60, through the threaded collar 50 (e.g., when threadedly released from the threaded portion 22 of the driving rod 20, and into the rod housing 24. The rod housing 24 may be capped by an end cap 27 held by a retaining pin 29 or other fastener. The non-threaded collar 60 is used to hold the first (fixed) arm and may be retained on the rod housing 24 with a pin 62 or other suitable fastener. The threaded collar 50 is used to hold the second (mobile) arm 40 and includes additional parts to enable a releasable threaded connection. In this example, the releasable threaded connection comprises the cam lever 54, a spring cap 56 and spring 58, and a threaded button 57. The threaded button 57 threadedly engages the threaded portion 22 of the driving rod 20 when urged downwardly by the cam lever 54, and releases from the threaded portion 22 of the driving rod 20 when urged away from the threaded portion 22 by the biasing action of the spring 58.

The arms are multi-segmented as discussed above. In this example, the first arm 30 includes arm segments 31, 32 and the second arm 40 includes arm segments 41, 42, which are pivotably coupled using screws 33, 43. The attachment members comprise the lockable swivels 90 and connector tips 35, 45, which cam levers 34, 44 to releasably lock in the desired swivel angle as discussed above. Again, other embodiments may be constructed with one or more of the optional adjustment features disclosed or variants thereof, all of which are considered within the scope of this disclosure.

The disclosed instrument in any of its embodiments may be used in a surgical method involving the manipulation of vertebrae. In one example method, distal ends of first and second arms of an instrument are releasably coupled to respective vertebrae, such as by using attachment members to couple connector tips to bone fasteners extending from vertebrae. Proximate ends of the first and second arms are rotatably coupled to a driving rod about an axis defined by a threaded portion of the driving rod. This connection may be facilitated by releasing a threaded collar from the threaded portion of the driving rod and sliding the second arm along the driving rod to position the second arm adjacent the respective vertebra. The threaded collar may be re-engaged with the threaded portion of the driving rod. The driving rod is then rotated with the threaded portion of the driving rod coupled with a threaded collar in axial engagement with the second arm, to translate the second arm along the driving rod with respect to the first arm. Thus, rotation of the driving rod may forcibly engage the respective vertebrae, as may be limited by an optional torque limiter.

In a modular system, coupling the arms to the vertebrae may comprise selecting one of a plurality of modular attachment members having different attachment member configurations interchangeably connectable to the bone fastener. The selected modular attachment member may then be used to couple a connector tip on the arm to the bone fastener. Each arm may be articulated with respect to the driving rod and rotated about a swivel to a selected swivel angle to better accommodate a variety of different anatomical variations between different patient spines.

Accordingly, the present disclosure may provide an apparatus, system, and method for manipulating selected vertebrae during a spinal procedure. The instrument may include various disclosed adjustment features to accommodate anatomical variations. The system may be a modular system allowing an instrument to be used across a range of different platforms.

Therefore, the present embodiments are well adapted to attain the ends and advantages mentioned as well as those that are inherent therein. The particular embodiments disclosed above are illustrative only, as the present embodiments may be modified and practiced in different but equivalent manners apparent to those skilled in the art having the benefit of the teachings herein. Although individual embodiments are discussed, all combinations of each embodiment are contemplated and covered by the disclosure. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of the present disclosure.

What is claimed is:

1. A method, comprising:
releasably coupling distal ends of first and second arms of an instrument to respective vertebrae, wherein proximate ends of the first and second arms are rotatably coupled to a driving rod about an axis defined by a threaded portion of the driving rod, the second arm having a threaded collar coupled to the threaded portion of the driving rod in axial engagement with the second arm;
releasably connecting, by a releasable threaded connection, the threaded collar and the threaded portion of the driving rod, the releasable threaded connection allowing for non-threaded axial re-positioning of the second arm along the driving rod when the threaded connection between the threaded collar and the threaded portion of the driving rod is released, the releasable threaded connection comprising a cam lever mechanism; and
after releasably connecting, rotating the driving rod with the threaded portion of the driving rod coupled with the threaded collar which is connected to the threaded portion, to translate the second arm along the driving rod with respect to the first arm,
prior to releasably connecting, further comprising:
sliding the second arm along the driving rod with the threaded collar released from the threaded portion of the driving rod to position the second arm adjacent the respective vertebra.

2. The method of claim 1, wherein releasably coupling the distal ends of first and second arms of an instrument to respective vertebrae comprises releasably coupling each arm to a bone fastener extending from the respective vertebra.

3. The method of claim 2, wherein releasably coupling each arm to the bone fastener comprises:
selecting one of a plurality of modular attachment members having different attachment member configurations interchangeably connectable to the bone fastener; and
using the selected modular attachment member to couple a connector tip on the arm to the bone fastener.

4. The method of claim 2, further comprising:
swiveling each arm about a swivel to a selected swivel angle and rotatably securing each arm to the respective bone fastener at the selected swivel angle.

5. The method of claim 4, further comprising locking each swivel at the selected swivel angle.

* * * * *